United States Patent [19]

Yoshida

[11] 4,277,802
[45] Jul. 7, 1981

[54] DEFECT INSPECTION SYSTEM
[75] Inventor: Hajime Yoshida, Tokyo, Japan
[73] Assignee: Hajime Industries, Ltd., Tokyo, Japan
[21] Appl. No.: 121,518
[22] Filed: Feb. 14, 1980
[30] Foreign Application Priority Data Feb. 20, 1979 [JP] Japan ............................ 54-18867

[51] Int. Cl.³ ............................................. H04N 7/18
[52] U.S. Cl. .................................... 358/106; 250/563; 356/394
[58] Field of Search ............... 358/106; 356/376, 388, 356/389, 390, 392, 394, 237; 250/262, 263, 272

[56] References Cited
U.S. PATENT DOCUMENTS 4,110,048  8/1978  Akutsu et al. .................. 250/563
4,163,991  8/1979  Burrig ............................ 358/106

Primary Examiner—Joseph A. Orsino, Jr.

[57] ABSTRACT

A defect inspection system which features the inspection of an object to be inspected by optically matching the lights from a standard subject and the inspected object, whereas, an image signal is formed by a monochrome television camera based upon, and by having a plurality of detection sections which output signals corresponding to the rate of changes of the image signal with respect to time, so that although all of the above mentioned detection sections output signals when the above mentioned standard subject and the inspected object match, when the above mentioned inspected object does not match the standard subject, some of the above mentioned detection sections shall output signals while the other detection sections shall not output signals by arrangements of the sensitivities of the above mentioned plurality of detection sections, so that a defect detection signal is output whenever some of the above mentioned detection sections output no signals.

4 Claims, 16 Drawing Figures

FIG. 5A
FIG. 5B
FIG. 5C
FIG. 5D
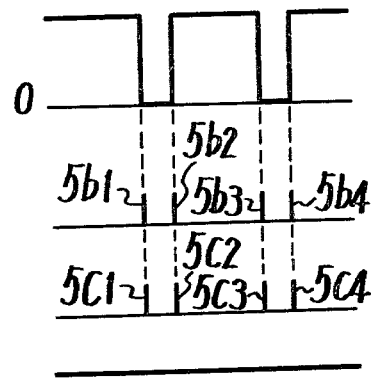
FIG. 6A
FIG. 6B
FIG. 6C
FIG. 6D
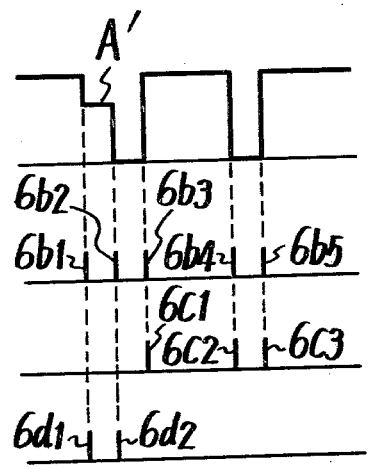
FIG. 7A
FIG. 7B
FIG. 7C
FIG. 7D
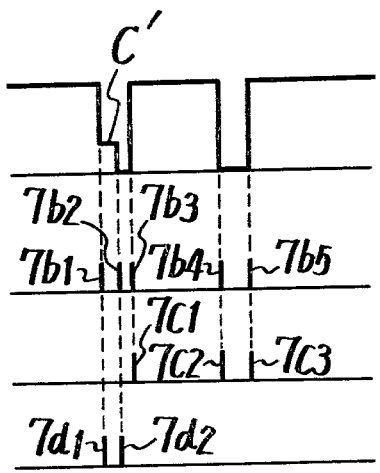

DEFECT INSPECTION SYSTEM

BACKGROUND OF THE INVENTION

1. Field of the Invention

The present invention generally relates to a defect inspection system and is directed more particularly to a defect inspection system which inspects the defects on patterns or the like of an object to be inspected.

2. Description of the Prior Art

It is a general practice to use photomasks which have a predetermined pattern upon manufacturing semi-conductors, printed circuit boards or the like. In such case, when there is a defect on the pattern of the photomask, it will cause the production of reject products so that the photomask pattern defect inspection is an important process in the art.

An example of a defect inspection system for patterns as proposed under the prior art shall be explained in reference with FIGS. 1, 2 and 3 hereunder.

FIGS. 1 and 2 are respectively plan views showing magnified photomask portions by a microscope on which 1 and 1' are respectively photomasks made of transparent material such as glass or the like, 2 and 2' are respectively patterns formed by evaporated metal or the like, in general on photomasks 1 and 1', 3 is the transparent section of the transparent base plate of photomasks 1 and 1', and 4 is the nontransparent or opaque portion of the photomasks 1 and 1' by the evaporated material thereon.

On FIG. 2, A and B are the portions at which the evaporated material unnecessarily remains, while C and D are the portions where the necessary evaporated material is lacking. Accordingly, photomask 1' which has a pattern such as 2' as shown on FIG. 2, is a defective product. On the other hand, the photomask 1 as shown on FIG. 1 is a complete and normal product.

In order to inspect photomasks such as 1 or 1' as shown on FIGS. 1 and 2 under the prior art, for instance as shown on FIG. 3, a standard mask 6 which has a complete pattern (for instance such as pattern 2 as shown on FIG. 1) is placed at a predetermined position on a transparent base 5 as an example, while a mask 7 to be inspected (such as a defective pattern 2' as shown on FIG. 2) is placed at another predetermined location on base 5, whereas both are observed by a binocular microscope 8. On FIG. 3, 9 and 10 are object lenses for both of the standard mark 6 and inspected mask 7, 11 and 12 are mirrors for both masks 6 and 7, 13 and 14 are half mirrors for both masks 6 and 7, 15 is a common eye piece lens, 16 is a light source for instance which irradiates red light on the standard mask 6, and 17 is the light source for a red complimentary colour such as a green light for instance, which irradiates on the mask 7 to be inspected. The lights emitted from light sources 16 and 17 pass through the base 5 of the binocular microscope 8, masks 6 and 7, lenses 9 and 10, mirrors 11 and 12, half mirrors 13 and 14, and further lens 15 and form a focussed image at an observing eye 18, which makes the inspection of a mask possible.

In the case that the inspected mask 7 is a defective product as shown on FIG. 2, at portions A and B, the green light from light source 17 is shielded by such portions A and B, while only the red light from light source 16 arrives at the observing eye 18, and hence such portions A and B appear in red colour. On the other hand, for portions C and D, the red light from light source 16 is shielded but the green light from light source 17 arrives at the observing eye 18 and accordingly, such portions C and D appear in green colour. As for the other portions such as the transparent portion 3, both of the red and green lights from light sources 16 and 17 arrive at the observing eye 18 simultaneously and hence the transparent portion 3 generally appear as white and further, as for the opaque section 4 the red and green lights are both shielded and do not pass and hence the opaque section 4 appears as black generally. In other words, when the entire mask appears in white or black, the inspected mask 7 has no defect and whenever there is a slight shade or red or green visible, the inspected mask 7 shall be a defective product.

The above mentioned defect inspection system for patterns under the prior art contains the fault that the inspection can not be automatically conducted because it is conducted at piece by piece with the human eyes. In the case that this inspection was to be automated, a very high costing colour television camera becomes necessary.

OBJECTS AND SUMMARY OF THE INVENTION

Accordingly, it is a main object of the present invention to present a defect inspection system which can automatically conduct the inspection of defects on an object to be inspected without using a high costing colour television camera, but with a low costing monochrome television camera.

According to an aspect of the present invention a defect inspection system by comparative inspection of a standard subject with an object to be inspected is provided which comprises:

(a) means for supporting a standard subject and an object to be inspected at predetermined positions, respectively;

(b) optical means for forming an overlapped image of said standard image and object;

(c) means for picking up said overlapped image and producing a video signal thereof;

(d) a plurality of detecting means connected to said picking-up means for producing signals in response to rate of change of said video signal with respect to time, sensitivity of said plurality of detecting means being so selected that when said standard subject and object coincide with each other, all of said plurality of detecting means produce signals, but when said object is different from said standard subject, some of said detecting means do not produce any signals while the remaining detecting means produce signals; and (e) means connected to said plurality of detecting means for producing a defect detection signal when some of said detecting means do not produce any signals but the remaining ones produce signals, namely said object is a defective one.

The additional, and other objects, features and advantages of the present invention will become apparent from the following description taken in conjunction with the accompanying drawings.

BRIEF DESCRIPTION OF THE DRAWINGS

FIGS. 5, 6 and 7 are respectively waveform diagrams in order to explain the example of the invention shown in FIG. 4.

DESCRIPTION OF THE PREFERRED EMBODIMENT

The present invention will be hereinafter described with reference to the attached drawings.

Figure 3:
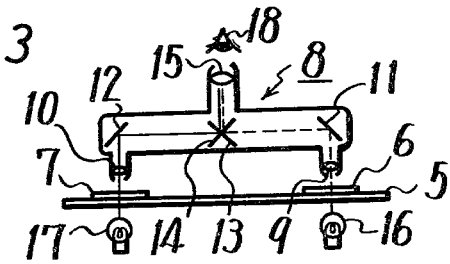
FIG. 3 is a schematic diagram of a pattern inspection system under the prior art.
Figure 4:
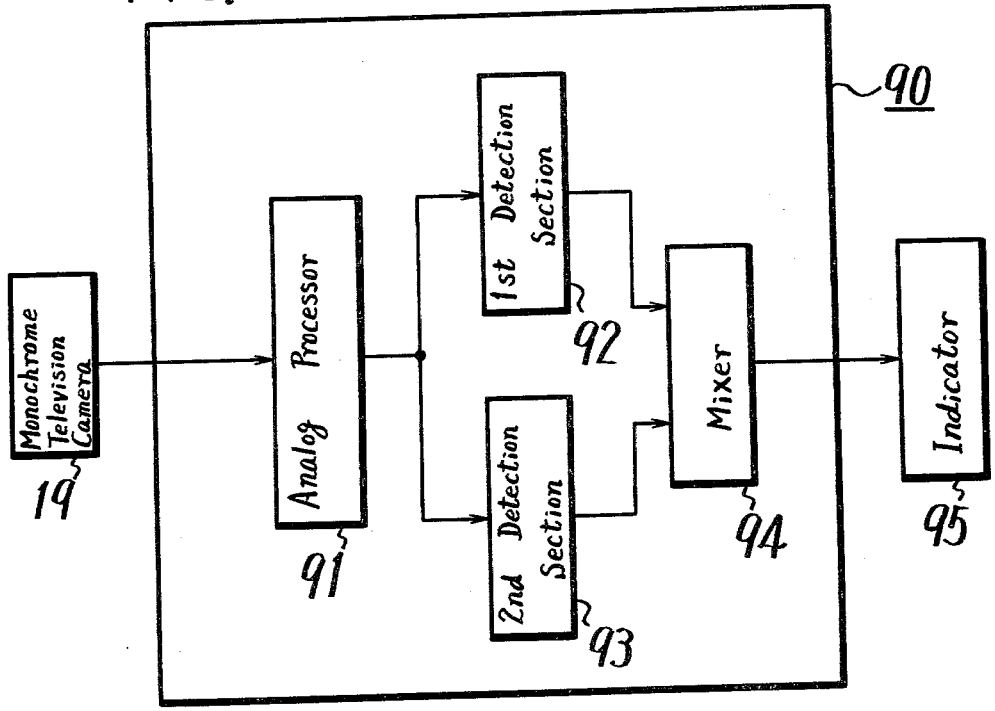
FIG. 4 is a block diagram showing one example of the present invention.

FIG. 4 shows a block diagram which illustrates one example of the defect inspection system under the present invention. In FIG. 4, 90 designates the defect detection assembly in general. In this example the defect detection assembly 90 corresponds to the observing eye 18 on FIG. 3. In other words, it includes an analog processor 91 made of, for example, an amplifier and a low pass filter which receives the video signal as an output from a monochrome television camera 19 which picks up an object to be inspected as well as a standard subject (both not shown in FIG. 4) and processes the same, 1st and 2nd detection sections 92 and 93, each made of, for example, a level comparator and one-shot multivibrator, which receive the output of the analog processor 91, and a mixer 94 such as an exclusive OR circuit which receives the outputs from both detection sections 92 and 93, and supplies its output to an indicator 95.

In the example of the present invention as above mentioned, the analog processing section 91 has the functions to receive the video or image signal from the monochrome television camera 19 and to amplify the image signal to an adequate level, as well as the function to remove the unnecessary components from the same. The 1st detection section 92 and the 2nd detection section 93, both respectively catch the rate of level change of the image signal with respect to time. In other words, for instance, the detection sensitivity of the 1st detection section 92 is selected high while the detection sensitivity of the 2nd detection section 93 is selected lower than the 1st detection section 92. The mixer 94 for instance has a function such as an exclusive logic circuit which does not produce an output when both the 1st detection section 92 and the 2nd detection section 93 and produces an output when either one of the detection sections does not generate an output. Indicator 95 indicates a defect based upon the supplied output signal from the mixer 94 when there is a defect on the inspected object, which is the time that an output is supplied from the mixer 94.

Figure 1:
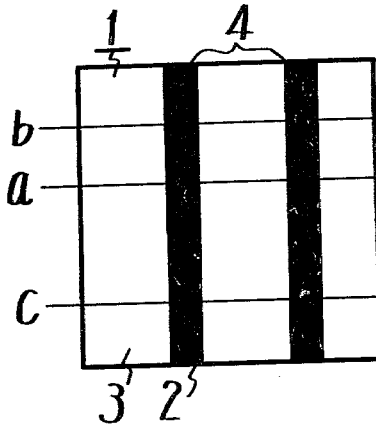
FIGS. 1 and 2 are respectively plan views of objects to be inspected which have a complete and defective pattern respectively.
Figure 2:
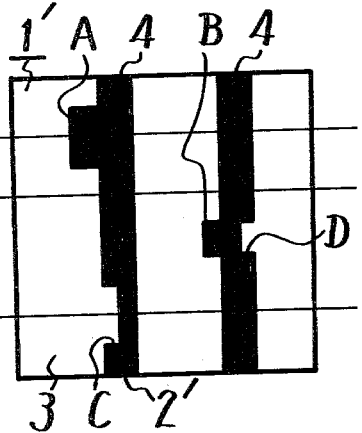

As the next step, an example of the function of the defect inspection system under the present invention as above mentioned shall be described in conjunction with an application to inspect such patterns as shown on FIGS. 1 and 2. In this case the monochrome television camera 19 on FIG. 4 is placed in lieu of the observing eye 18 on FIG. 3. The picked up output, in other words, the image signal from the television camera 19 is only a certain level of white or black as shown on FIG. 5A, when the inspected pattern 7 is a complete product (for instance, as shown on FIGS. 1 and 2, corresponding to the one horizontal period as shown with line a), but when there are surplus protruding portions such as A or B portions as shown on FIG. 2 on the inspected pattern 7 (for instance, corresponding to the one horizontal period shown as line b on FIGS. 1 and 2), the image signal becomes levels of white and black including a half level A' or level therebetween as shown as FIG. 6A, and further when there are portions on the inspected pattern 7 with material lacking such as C and D of FIG. 2 (for instance, corresponding to one horizontal period as shown as line c on FIGS. 1 and 2), the image signal becomes levels of white and black including another half level C' or level therebetween as shown on FIG. 7A.

The 1st detection section 92 as well as the 2nd detection section 93 which receive the output from the analog processor 91 which receives and processes the output of television camera 19, as above mentioned, catch the rate of level changes of the image signal with respect to time, and both are arranged to have different detection sensitivities. Therefore, when the television camera 19 delivers the image signal with the waveforms such as shown on FIGS. 5A, 6A and 7A, the detection sections 92 and 93 deliver detection output pulse signals such as 5b1, 5b2, 5b3, 5b4; 6b1, 6b2, 6b3, 6b4, 6b5; 7b1, 7b2, 7b3, 7b4, 7b5 and 5c1, 5c2, 5c3, 5c4; 6c1, 6c2, 6c3; 7c1, 7c2, 7c3, respectively, as shown on FIGS. 5B, 6B, 7B and 5C, 6C, 7C. In other words, while the 1st detection section 92 produces the pulse signals in response to all of the rising-up and falling-down of the image signal, the 2nd detection section 93 produces no output pulse signals at the portions responding to the half level portions A' and C' of the image signal while the pulse signals at the other portions are output in the same manner as the 1st detection section 92.

At the mixer 94, which receives the outputs from both the 1st and the 2nd detection sections 92 and 93, when the output pulse signals from both detection sections 92 and 93 are presented in coincidence, in other words, when the inspected pattern is a complete product, no output is produced as shown on FIG. 5D. Further, when one detection section, for instance in this example the 2nd detection section 93 does not output a pulse signal, while only the other inspection section, which is the 1st detection section 92, outputs a pulse signal, in other words, when there is a defect on the inspected pattern, defect detection signals such as pulse signals 6d1, 6d2 as well as 7d1, 7d2 are respectively output from the mixer 94 as shown on FIGS. 6D and 7D. In other words, at section A' of the image signal which responds to the defect A on the inspected pattern, as shown on FIGS. 6B and 6C, while the 1st detection section 92 outputs pulse signals 6b1 and 6b2, the 2nd detection section 93 does not output any pulse signal, so that the mixer 94 outputs pulse signals 6d1, 6d2 as shown on FIG. 6D. In this same respect, at portions C' of the image signal which corresponds to the defect portion C of the inspected pattern, as shown on FIGS. 7B and 7C, while the 1st detection section 92 outputs pulse signals 7b1, 7b2, the 2nd detection section 93 does not output any pulse signal, so that mixer 94 outputs pulse signals 7d1, 7d2 as shown on FIG. 7D. In other words, only when there are defects such as A, B, C and D as shown on FIG. 2, on the inspected pattern, the mixer 94 outputs a defect detection signal in the form of pulse signals. Therefore, by supplying the output of the mixer 94 to the indicator 95 such as a lamp, a buzzer or the like, when the inspected pattern is a defective product, the defect detection indication can be automatically conducted.

Further, although not shown on the drawings, the output of the mixer 94 can be amplified to drive the inspection system so that defective products can automatically be segregated.

As explained above, by the present invention, a major effect is presented by which the inspection of whether a defect exists or not on the inspected pattern can be automatically conducted, and further, by utilizing the defect detection signals, it is a simple matter to segregate the complete products and defect products of the inspected pattern.

It is noted that in the above example, while the inspection of a pattern which is formed by evaporated metal on a transparent base plate is applied and explained, in the case of a pattern formed on an opaque base plate for an example, reflected light from the same may be used and the latter example may be applicable in the same manner to the present invention.

The above description is given on a single preferred embodiment of the present invention, but it will be apparent that many modifications and variations could be effected by one skilled in the art without departing from the spirits or scope of the novel concepts of the invention.

I claim as my invention:

1. A defect inspection system by comparative inspection of a standard subject with an object to be inspected comprising:
   (a) means for supporting a standard subject and an object to be inspected at predetermined positions, respectively;
   (b) optical means for forming an overlapped image of said standard image and object;
   (c) means for picking up said overlapped image and producing a video signal thereof;
   (d) a plurality of detecting means connected to said picking-up means for producing signals in response to rate of change of said video signal with respect to time, the sensitivity of said plurality of detecting means being so selected that when said standard subject and object coincide with each other, all of said plurality of detecting means produce signals, but when said object is different from said standard subject, some of said detecting means do not produce any signals while the remaining detecting means produce signals; and
   (e) means connected to said plurality of detecting means for producing a defect detection signal when some of said detecting means do not produce any signals but the remaining ones produce signals, namely said object is a defective one.

2. A defect inspection system according to claim 1 further including means connected to said last-mentioned means for indicating an alarm when said object is a defective one.

3. A defect inspection system according to claim 1 further including means connected between picking-up means and detecting means for amplifying said video signal and removing unnecessary components thereof.

4. A defect inspection system as claimed in claim 1, in which said picking-up means is a monochrome television camera.

* * * * *